United States Patent [19]

Kompelien

[11] 4,225,791
[45] Sep. 30, 1980

[54] OPTICAL SMOKE DETECTOR CIRCUIT
[75] Inventor: Arlon D. Kompelien, Richfield, Minn.
[73] Assignee: Honeywell Inc., Minneapolis, Minn.
[21] Appl. No.: 16,697
[22] Filed: Mar. 1, 1979
[51] Int. Cl.³ .......................................... H01J 40/14
[52] U.S. Cl. ........................... 250/574; 250/214 AG
[58] Field of Search ............ 250/576, 214 AG, 214 R; 356/338; 340/630

[56] References Cited
U.S. PATENT DOCUMENTS

| | | |
|---|---|---|
| 3,185,975 | 5/1965 | Kompelian . |
| 3,940,753 | 2/1976 | Muller . |
| 4,063,227 | 12/1977 | Peterson . |

Primary Examiner—David C. Nelms
Assistant Examiner—Darwin R. Hostetter
Attorney, Agent, or Firm—Omund R. Dahle

[57] ABSTRACT

An improved circuit for an optical smoke detector utilizing an active band pass filter which has a bias feedback to the phototransistor detecting element to bias the phototransistor to a static conductivity state of high gain or high sensitivity without regard to whether the phototransistor is in a high ambient light level or a low (dark) ambient light level.

4 Claims, 3 Drawing Figures

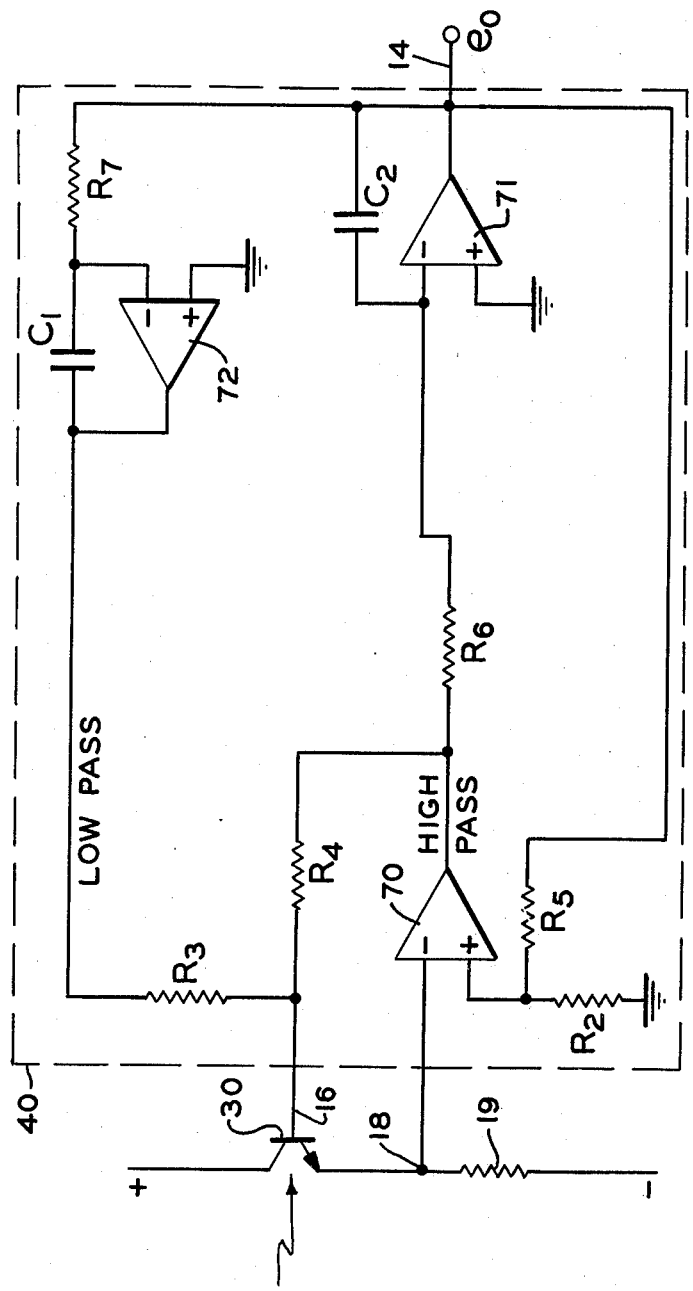
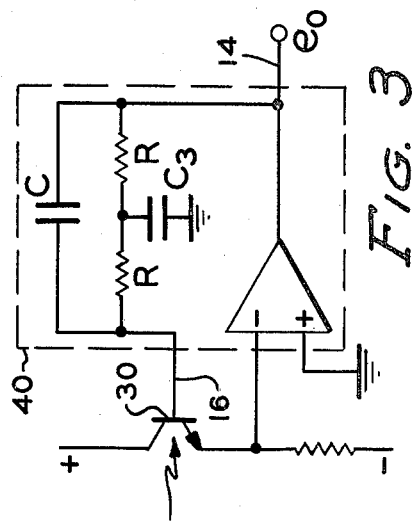
FIG. 2
FIG. 3

OPTICAL SMOKE DETECTOR CIRCUIT

BACKGROUND OF THE INVENTION

This invention relates to the field of electronic optical smoke detectors. Prior art optical type techniques for detecting smoke require specially designed chambers for the passage of smoke filled air. These chambers are designed to minimize high ambient lighting situations. Some of these chambers require long airflow pathways to minimize the ambient lighting effects. These long path chambers cause attentuation of the actual smoke signal. Thus, the sensitivity of the smoke chamber is lessened.

SUMMARY OF THE INVENTION

The smoke detector apparatus of this invention includes a pulsed light source and a phototransistor detector. The detector is incorporated in the feedback path of a band pass filter which controls the bias to the phototransistor. The output of the band pass filter is fed into a synchronous detector combined with a low pass filter to provide a very narrow band pass for excellent frequency selection. The apparatus sensitivity is not affected by the magnitude of ambient light level at the detector.

It is an object of the invention to provide an electronic circuit for maintaining the sensitivity of the phototransistor in both high and low (dark) ambient lighting conditions.

It is an object of this invention to provide an electronic light sensing circuit and a light source circuit which obviates the need for long airflow path chambers and is impervious to ambient lighting conditions.

BRIEF DESCRIPTION OF THE DRAWINGS

FIG. 2 is a schematic diagram of a preferred embodiment of a portion of the circuit of FIG. 1.

FIG. 3 is another embodiment from that shown in FIG. 2.

DESCRIPTION

Figure 1:
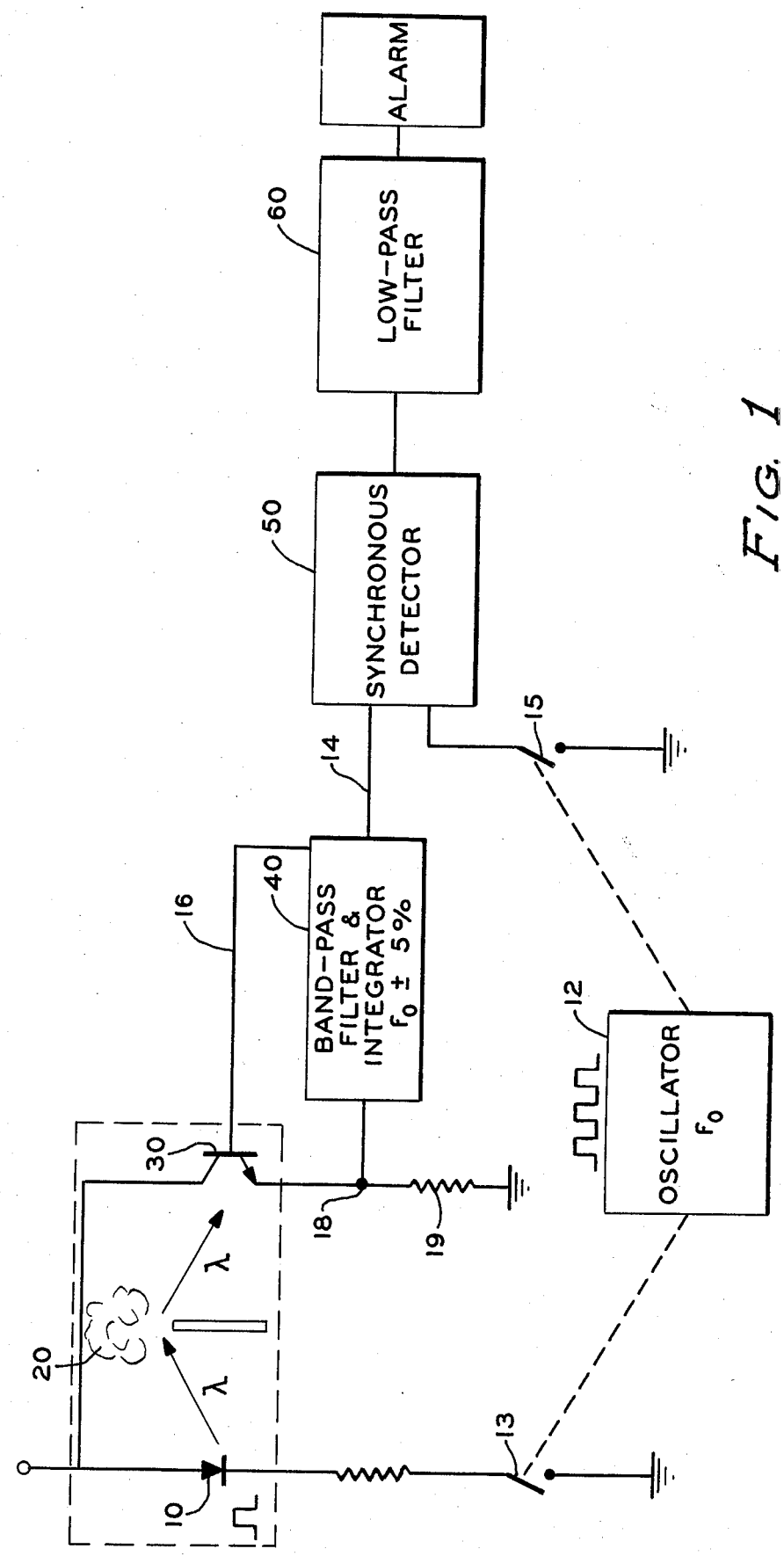
FIG. 1 is a system schematic representation of the smoke detector and is partially in block diagram form.

There is described herein an improved smoke detector of the photo-electric type. The smoke detector includes a pulsating light source and a phototransistor light detector. The light detector is connected in the feedback path of a band pass filter. The band pass filter provides not only the band pass frequency but also provides an automatic gain control for the light detector. The automatic gain control is effective to maintain a high and uniform sensitivity of the smoke detector over wide ranges in light intensity from conditions of high intensity ambient lighting to conditions of low (near dark) intensity ambient lighting. It is desirable that the system have a uniform sensitivity to smoke under varying ambient light conditions. In a phototransistor it has been found that with very little emitter current such as normally may tend to exist at a low level of ambient lighting, the transistor has low gain, i.e. low sensitivity. By this improved circuit design to force an increase in the phototransistor current at low ambient light levels, the sensitivity is maintained high. In addition, at high ambient light levels, the phototransistor may tend to saturate, i.e. the emitter current may be high. Again, the improved bias circuit design prevents the phototransistor from saturating, thereby maintaining the sensitivity to smoke.

The smoke detector system is broadly shown in FIG. 1, in which a light emitting diode (LED) 10 provides a pulsing light source to a smoke sensing chamber 20. The chamber 20 has adequate openings to allow the ambient air of the area or room being protected to enter the sensing chamber. A phototransistor 30 in the sensing chamber is arranged and positioned to detect the pulsing LED light when it is reflected from smoke which has entered the chamber. As an example, such a chamber in which reflected light reaches the detector is shown in my U.S. Pat. No. 3,185,975. The pulsing light source 10 is controlled by the oscillator 12 of frequency $f_o$ (which may be 1000 hz, for example). LED 10 and the collector electrode of phototransistor 30 are both energized from a positive DC source, the energization of LED 10 being interrupted at the frequency $f_o$ of the oscillator 12 by the switching means 13. When there is smoke in the chamber 20 to reflect the pulsing light towards sensor 30, the sensor will see a signal at the frequency $f_o$. The phototransistor 30 is connected in the feedback loop at the input of an active amplifier in band pass filter 40 which filter also has a secondary function as an integrator. Specifically, a feedback lead 16 of the band pass filter 40 is connected to the control electrode of the phototransistor 30. The emitter of phototransistor 30 is shown as connected by a junction 18 and a resistor 19 to ground, and the phototransistor emitter at the junction 18 is connected to the input of filter 40. The output of the band pass filter 40 is also fed into the synchronous detector or demodulator 50. The synchronous detector is synchronized with the pulsing light source 10 at frequency $f_o$ by the oscillator 12. The generally shown switching points 13 and 15 may be suitable solid state switches. The output of the synchronous detector is fed into a low pass filter 60, the output of which in turn is connected to an alarm circuit. The band pass filter 40 has a relatively larger band pass than that derived from synchronous detector 50 and low pass filter 60 which is very selective (such as $f_o \pm 0.1\%$) to the frequency of oscillator 12. Signals at frequencies $f_o$ to the input of the synchronous detector translate to DC at the output of the low pass filter 60.

A more specific embodiment of the active filter portion of FIG. 1 is shown in the schematic presentation of FIG. 2 which utilizes a conventional active filter with a novel and unique way of coupling a phototransistor into the input. The filter, per se, generally similar to that shown in FIG. 2 is sometimes called a state variable filter or biquad amplifier and is well known in the art. The active band pass filter shown in FIG. 2 comprises operational amplifiers 70, 71 and 72. A dual source, positive and negative, with respect to ground energizes this circuit allowing the outputs of the operational amplifiers to move positive or negative. Junction 18 is connected to the negative input of amplifier 70, the positive input of which is connected through a resistor $R_2$ to ground. A feedback resistor $R_4$ from the output of amplifier 70 is connected to the base electrode of phototransistor 30. This portion of the active filter provides a high pass output. The amplifier 70 output is also connected through a resistor $R_6$ to the negative input of amplifier 71, the other input thereof being connected to ground. A feedback capacitor $C_2$ is connected from amplifier 71 output 14 to its negative input. Another feedback circuit path connects the output of amplifier 71 through a resistor $R_5$ to the positive input of amplifier 70. $R_5$ is selected to provide the proper band width of the band pass filter. Output 14 is also connected through a resistor $R_7$ to the negative input of an amplifier 72 the positive input of which is connected to ground. A feedback capacitor $C_1$ connects the output of amplifier 72 to its negative input terminal. The amplifier 72 output is also connected by a resistor $R_3$ to the base electrode of phototransistor 30. The feedback lead 16 (FIG. 1) is in the embodiment of FIG. 2 made up of signals from feedback resistors $R_3$ and $R_4$. The base current of phototransistor 30 is the sum of the current flowing through $R_4$ and current flowing through $R_3$. The DC currents flowing through $R_3$ and $R_4$ maintain the phototransistor's sensitivity to light to be a constant. In effect, the DC emitter current is kept constant. At the same time, amplifiers 70, 71 and 72 provide the necessary band pass filter operation, and the output 14 provides a band pass output $e_o$ from the active filter.

Consider the operation of FIG. 2 when the phototransistor is operating at steady state. That is, phototransistor 30 is receiving a finite amount of ambient light and the currents through $R_3$ and $R_4$ are at a constant. Also assume that the output voltage $e_o$ at 14 is at a finite value. If the ambient light that phototransistor 30 receives increases, the phototransistor emitter current (DC) will tend to increase and the resulting DC voltage change into the negative input of amplifier 70 will cause the output of amplifier 70 to decrease. The decrease in output voltage of amplifier 70 will cause the current flowing through $R_4$ to also decrease. This, in turn, will tend to cause the voltage at 18 to decrease. Thus, a negative feedback circuit is provided by $R_4$ around the operational amplifier 70 to tend to maintain constant emitter current of the phototransistor when there is either an increase in ambient light or a decrease in ambient light. At the same time as the negative feedback current above is operating, operational amplifier 71 sees the change in output from amplifier 70. The voltage $e_o$ will increase and cause operational amplifier 72 to cause a decrease in voltage. The decrease or falling in voltage at the output of amplifier 72 will tend to lessen the current flowing through resistor $R_3$ and subsequently cause the current flowing through the base of phototransistor 30 to also tend to decrease. This decrease in base current also causes the voltage at 18 to decrease. Thus, a second negative feedback path for DC changes is provided. Also in very dark ambient lighting, phototransistor (DC) current will be forced by current through $R_3$ and $R_4$. Transistors with very little emitter current have low gain. Forcing this phototransistor current up, in dark conditions, maintains high sensitivity. The net effect of operational amplifiers 71, 72 and 70 tend to cause the voltage at point 18, at the input of operational amplifier 70, to remain near ground potential. Thus, in this improved smoke detector circuit the described feedback to the base of the phototransistor 30 is effective to automatically adjust its base bias to maintain its emitter near ground potential over very large ambient light conditions (i.e. average phototransistor emitter current is a constant). A constant emitter current regardless of ambient lighting maintains the gain or sensitivity of the phototransistor to be nearly constant since sensitivity is a function of emitter current.

Because the phototransistor 30 responds to the sum of currents flowing through $R_3$ and $R_4$ as in the conventional active filter amplifier circuit of FIG. 1, the circuit of FIG. 2 acts as an active filter when the phototransistor is responding to a pulsating light at the central band pass frequency. Thus, when smoke is present the phototransistor will be responding to the pulsating light at the central band pass frequency $f_o$.

A pulsating signal at the band pass frequency $f_o$ will be at the output $e_o$. The active filter will not attenuate the base current at phototransistor 30 at the band pass frequency since the A.C. components of current in $R_3$ and $R_4$ cancel each other (i.e. 180° out of phase). The integrator action of each of operational amplifiers 71 and 72 provides the 180° phase shift at the frequency $f_o$. Light pulse signal currents from the phototransistor at the band pass frequency $f_o$ produce the signal that is amplified and supplied to the band pass output $e_o$.

Although FIG. 2 shows the preferred circuit embodiment for use in the invention, another embodiment is shown in FIG. 3. In this alternate embodiment, a different form of active filter design is used, however, this general band pass filter type is well known in the art. With the phototransistor in the feedback loop of the amplifier, the circuit of FIG. 3 behaves essentially in the same manner as that of FIG. 2. Here the feedback lead 16 (FIG. 1) is the embodiment of a signal from the bridge T RC feedback network. The two resistors in this network provide the DC component of current to maintain the constant emitter current of phototransistor 30.

The embodiments of the invention in which an exclusive property or right is claimed are defined as follows:

1. Optical smoke detector apparatus comprising:
   a source of light pulses having a pulse rate of $f_o$ within a smoke sensing chamber;
   phototransistor light pulse sensing means in said chamber, said phototransistor having collector, emitter and base electrodes, said phototransistor being energized by a DC source connected to said collector electrode;
   a resistance connected from said emitter electrode to a reference potential, said phototransistor providing electrical pulses at said emitter corresponding to the sensed light pulses;
   a band-pass active filter tuned to the pulse rate frequency $f_o$, and having an input terminal connected to said emitter electrode to receive electrical pulse signals from said phototransistor, and having an output terminal for transmitting the electrical pulse signals to utilizing apparatus and;
   means for maintaining constant the phototransistor gain comprising a phototransistor bias and low pass current feedback path connected from said band pass filter to said base electrode to maintain substantially constant the DC emitter current over wide ranges of ambient light to which the phototransistor is exposed.

2. Optical smoke detector apparatus comprising:
   a smoke sensing chamber having openings in said chamber to allow access of the air in the room being monitored into said chamber;
   a light emitting diode in said chamber; means for pulse energizing said light emitting diode at a pulse rate frequency $f_o$ to produce light pulses;
   a phototransistor in said chamber for sensing said light pulses when there is smoke in said chamber, said phototransistor having collector, emitter and base electrodes;
   an active band pass filter tuned to the pulse rate frequency $f_o$, said filter having an input terminal connected to said emitter electrode to receive electrical pulse signals from said phototransistor, said filter also having an output terminal;

bias circuit means connected from said filter to said base electrode to bias said phototransistor into a relatively constant conductive state even when no ambient light falls on said phototransistor so that high gain and sensitivity of said phototransistor is maintained irrespective of the level of ambient light falling on said phototransistor.

3. The apparatus according to claim 2 wherein said active band pass filter comprises:

first, second and third operational amplifiers, an input of the first operational amplifier being connected to said emitter electrode, the output of said first operational amplifier having a feedback resistor connected to said base electrode whereby the first operational amplifier of said filter operates as a high pass section;

said second operational amplifier having an input connected by a resistor to the first operational amplifier output, said second amplifier having an output connected to said output terminal and said output also connected through a feedback capacitor to the second amplifier input whereby the second operational amplifier of said filter operates as a low pass section;

said third operational amplifier having an input connected by a resistor to said second operational amplifier output;

said third amplifier having an output connected by a feedback resistor to said base electrode for providing a bias current to said phototransistor, said third amplifier also having a feedback capacitor from its output to its input whereby said third operational amplifier operates as a low-pass section.

4. The apparatus according to claim 3 in which the total of the currents to the phototransistor base electrode from the two feedback resistors adjusts to maintain the DC emitter current essentially constant under all ambient light conditions at the phototransistor.

* * * * *